United States Patent
Ramjit et al.

(10) Patent No.: US 9,326,884 B2
(45) Date of Patent: May 3, 2016

(54) OSTOMY DEVICE

(75) Inventors: Ravi Ramjit, Orangeburg, NY (US); Ta Kang Keng, Orangeburg, NY (US)

(73) Assignee: Euromed Inc., Orangeburg, NY (US)

( * ) Notice: Subject to any disclaimer, the term of this patent is extended or adjusted under 35 U.S.C. 154(b) by 0 days.

(21) Appl. No.: 13/332,039

(22) Filed: Dec. 20, 2011

(65) Prior Publication Data

US 2012/0220965 A1 Aug. 30, 2012

Related U.S. Application Data

(60) Provisional application No. 61/424,899, filed on Dec. 20, 2010.

(51) Int. Cl.
 *A61F 5/44* (2006.01)
 *A61F 5/443* (2006.01)
(52) U.S. Cl.
 CPC ..................................... *A61F 5/443* (2013.01)

(58) Field of Classification Search
 CPC ................. A61F 5/443; A61F 5/445; A61F 5/2005–5/4455; A61F 5/448; A61F 2005/4483; A61F 5/441; A61F 2005/4415; A61F 2005/4455
 USPC .................................................. 604/332–344
 See application file for complete search history.

(56) References Cited

U.S. PATENT DOCUMENTS

| | | | | |
|---|---|---|---|---|
| 3,805,789 | A * | 4/1974 | Marsan | 604/336 |
| 6,332,879 | B1 * | 12/2001 | Nielsen et al. | 604/344 |
| 8,211,073 | B2 * | 7/2012 | Dove et al. | 604/342 |
| 2003/0093042 | A1 * | 5/2003 | Leisner et al. | 604/337 |

* cited by examiner

*Primary Examiner* — Philip R Wiest
(74) *Attorney, Agent, or Firm* — Morgan Lewis & Bockius LLP

(57) ABSTRACT

A convex ostomy device, including i) a moldable pressure-sensitive thin center region covered on both sides with an adhesive; and ii) a thick region outside of and thicker than the center region, covered on both sides with the adhesive.

8 Claims, 3 Drawing Sheets

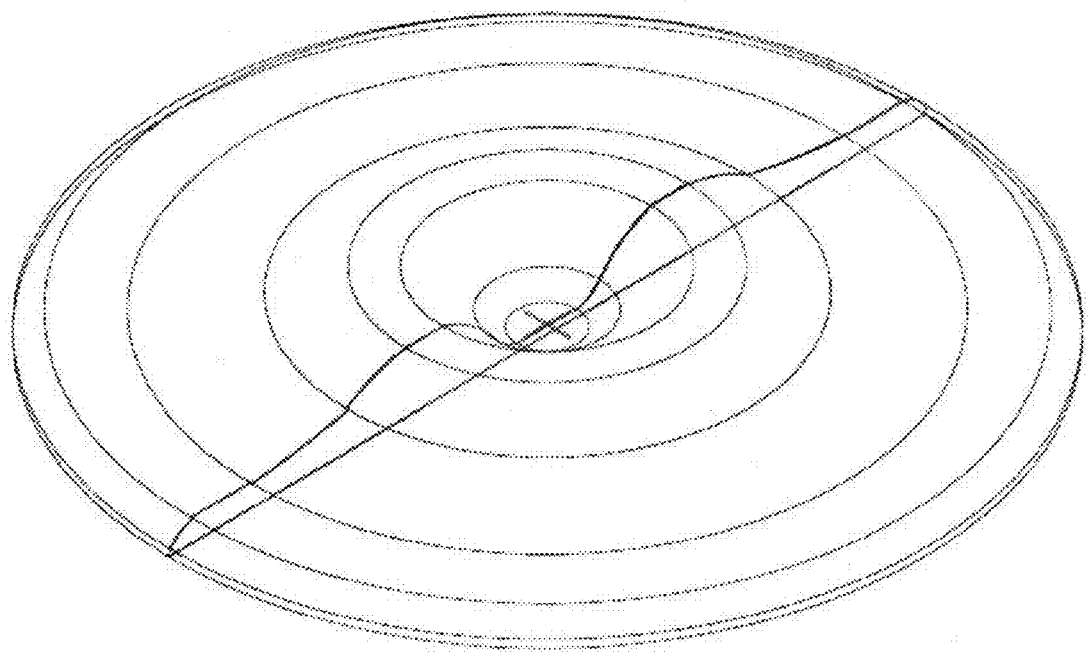
Figure 1. Ostomy wafer with pre-molded shape (isometric view)

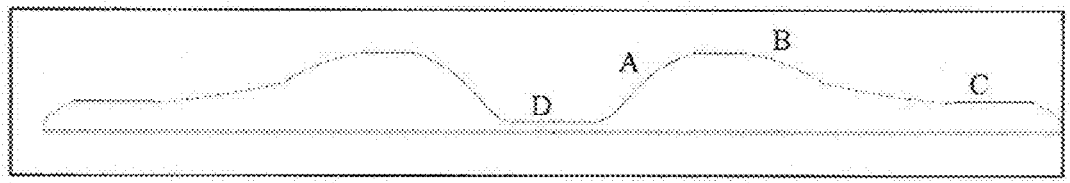

Figure 2. Ostomy wafer with pre-molded shape (cross section view)

A – Continuous indent allowing the stoma to penetrate through
B – Pre-raised neck portion allowing good seal around the stoma
C – This is the border region, with a tapered portion allowing conformability to the skin
D – This is the thin center region, which, in certain embodiments, can be pre-cut or embossed with cross pattern or slits allowing easy stoma penetration (Not shown in the side view)

OSTOMY DEVICE

CROSS-REFERENCE TO RELATED APPLICATIONS

The present application claims the benefit of U.S. provisional patent application 61/424,899, filed on Dec. 20, 2010, which is herein incorporated by reference in its entirety.

FIELD OF THE INVENTION

This invention relates to an ostomy device and its medical application.

BACKGROUND OF THE INVENTION

Conventional adhesive devices used in ostomy care are usually barrier sealed pouches. Typically, a layer of sealing barrier is applied to a stoma or wound, followed by a wafer on top of the stoma/wound. The products available on the market tend to have problems, such as fluid leakage where the skin around the stoma is irregular, or where folds of skin occur in these areas. Although a number of ostomy paste compositions have been used in an attempt to overcome these problems, the low viscosity of the paste makes its application messy and difficult.

Notwithstanding the various efforts directed towards developing ostomy compositions that might provide useful sealing around a stoma or wound, there remains a need to provide a more reliable and functional product which can minimize leakage upon application to the skin.

An important object of the invention is to provide such a device. Other objects will also be apparent from the following.

SUMMARY OF THE INVENTION

Broadly stated, the present invention provides an ostomy device which overcomes many of the prior art problems and allows for a simplified technique for applying the device to the skin. Specifically, the present ostomy device achieves excellent coverage of the stoma, and can be securely attached with the skin carrier through an easy application without using any ostomy paste.

BRIEF DESCRIPTION OF THE FIGURES

FIG. 1 is an isometric view of the ostomy device with a pre-molded shape according to the invention.

FIG. 2 is a cross section view of the ostomy device with a pre-molded shape according to the invention.

DETAILED DESCRIPTION OF THE INVENTION

Figure 3:
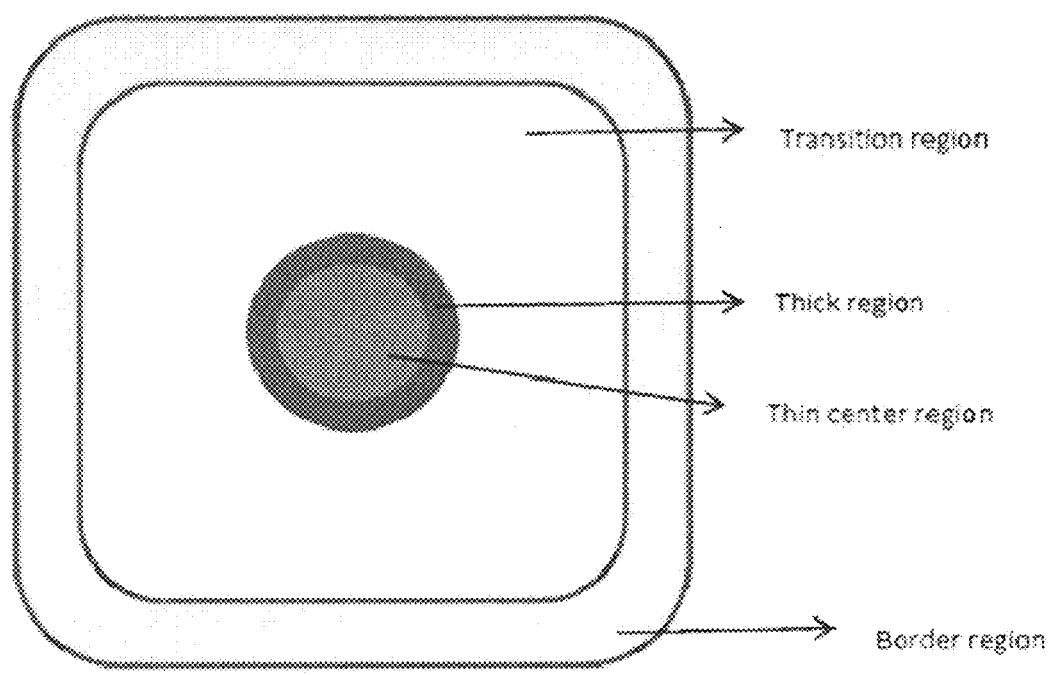
FIG. 3 is a top view of the ostomy device according to the invention.

In one embodiment, the invention relates to a convex ostomy device, including: i) a pressure-sensitive thin center region having a thickness of about 0.1 mm to about 0.5 mm and covered on both sides with an adhesive; and ii) a thick region outside of and thicker than the center region, having a thickness of about 0.5 mm to about 3 mm and covered on both sides with the adhesive. In certain embodiments, the thick region has a thickness of at least about 1 mm greater than the center region.

In an embodiment of the invention, the adhesive is a hydrocolloid adhesive. The hydrocolloid adhesive can further comprise a therapeutic material and/or the one or more accelerators.

In an embodiment of the invention, the thin center region is perforated.

In an embodiment of the invention, the ostomy device further comprises a border region outside of the thick region, said border region having a width of at least about 1 mm and having a thickness of at least about 0.2 times and less than 0.75 times that of the thick region.

In an embodiment of the invention, the device further comprises a skin protective additive.

As previously noted, in one embodiment the adhesive is a hydrocolloid. The hydrocolloid adhesive can comprise a water insoluble polymer such as cellulose. In one embodiment, the hydrocolloid adhesive comprises an aqueous mixture of a radiation crosslinkable water-soluble polymer, such as a polymer of N-vinyl-2-pyrrolidone, ethylene oxide and a humectant such as propylene glycol.

In one embodiment, the hydrocolloid adhesive comprises polyvinyl pyrrolidone and polyvinyl alcohol, a polar plasticizer or humectant such as propylene glycol, mineral oil, glycerol and water. The hydrocolloid adhesive may also contain cellulose derivatives to increase strength and compounds such as guar gum to increase tackiness.

In one embodiment, the hydrocolloid adhesive comprises a water-absorbent resin such as a vinyl acetate-acrylic acid ester copolymer that swells to form a hydrogel upon contact with water. In this embodiment, the adhesive may comprise a gelling agent, wherein the gelling agent comprises, for example, methylcellulose, a natural gum, glucose, propylparben, methylparaben, and sodium chloride. In other embodiments, the hydrocolloid adhesive of the present invention may further comprise a substituted urea. The hydrocolloid adhesive may further comprise coloring, fragrance or other pharmaceutically acceptable additives. Examples include but are not limited to pectin, alginates, vitamin E, and gelatin.

Additionally, the hydrocolloid adhesive may also contain therapeutic materials such as antibiotics or growth factors and silver sulfadiazine or other antibacterial products. The hydrocolloid composition may also include one or more accelerators to promote release of the antibacterial products. One type of accelerant is a surfactant.

Additionally, the ostomy device may also contain a skin protective additive. Examples of the skin protective additive include but are not limited to Soybean (Glycine Soja) Oil, *Sesamum Indicum* (Sesame) Oil, Safflower (*Carthamus Tinctorius*) Oil, Isopropyl Myristate, Cocoa Butter, Tocopheryl Acetate (Vitamin E).

Additionally, the thin center region, the thick region and the optional, the transition region and the border region can be of any of the geometrical shapes which include but are not limited to triangle, square, rectangle, parallelogram, trapezoid, circle, ellipse, and sector. The size of the shape can independently have a radius (where appropriate) roughly from about 0.1 mm to about 120 mm for the thin center region, from about 0.1 mm to about 160 mm for the thick region, and from about 1 mm to about 250 mm for the transition region. The width of the border region is at least about 1 mm.

The present adhesive device provides for a rapid uptake of stoma exudate and/or other body fluids. As used hereinafter the term "body fluid" shall include all fluids which are produced by and/or emanate from the body including, but not limited to stoma exudate. If the body fluid is not rapidly removed by the ostomy dressing, there is a tendency for the body fluid to pool on the surface of the wound or the surrounding skin under the dressing. As a result, the healing process is inhibited and healthy peri-stomal skin may be macerated, damaged, and infected by bacteria because of prolonged contact with moisture. Accordingly, the present invention can improve the healing process significantly with the absorbing, gelling, and gel induced water blocking feature of the composition.

One use or application of the present adhesive device is to function as an improved sealant to a stoma or wound. For example, the present adhesive device can be applied to a stoma with a good seal around the neck of the stoma. The thin center portion of the adhesive device can be broken with finger pressure along the pre-slit or embossed cross or star pattern slits allowing the stoma to penetrate. The broken thin center portion can be rolled up and molded toward the outer part of the device. The adhesive composition in the thin center portion with the rest of the pre-raised neck portion can further function to absorb and gel the exudated fluid, thus preventing it from spreading to other areas of skin. This design protects fluid from seeping through crevices and onto healthy skin. The thin region breaks upon mild applied pressure and can also be easily broken with gentle pressure from the stoma.

FIG. 1 presents an isometric view of the ostomy device (also referred to as an ostomy wafer). FIG. 2 shows the same ostomy wafer with a pre-molded shape in the cross sectional view. Region D is the moldable, tearable pressure-sensitive thin center region having a thickness of about 0.1 mm to about 0.5 mm and covered on both sides with an adhesive. By "tearable," it is meant that the region can be easily torn with finger pressure or the equivalent. The thick region of the device can be found between A and B of FIG. 2. The region between B and C is the transition region. Region C is the border region FIG. 3 provides a top view of the ostomy device, clearly showing the thin center region, the thick region, and the transition region and the border region.

The material used for the ostomy device is not particularly limited. In certain embodiments, for example, Kraton high performance elastomers are used as the wafer material.

The ostomy device described herein may be manufactured using traditional methods of manufacture. For example, Jensen, U.S. Pat. No. 5,133,821 and Samuelsen, U.S. Pat. No. 4,867,748 describe methods that may be used to manufacture the device.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

The invention claimed is:

1. A convex ostomy device, comprising
   i) a pressure-sensitive thin center region having a thickness of 0.1 mm to 0.5 mm and covered on both surfaces with an adhesive; and
   ii) a thick region outside of and thicker than the center region, having a thickness of 0.5 mm to 3 mm and covered on both surfaces with the adhesive,
   wherein the thin center region does not contain an opening;
   wherein the thin center region can be broken with finger pressure, and
   wherein the broken thin center portion can be rolled up and molded toward the outer part of the device.

2. The ostomy device of claim 1, wherein the adhesive is a hydrocolloid adhesive.

3. The ostomy device of claim 1, wherein the thick region has a thickness of at least 1 mm greater than the center region.

4. The ostomy device of claim 1, further comprising a transition region outside of the thick region, said transition region being thinner than the thick region.

5. The ostomy device of claim 4, further comprising a border region outside of the transition region, said border region having a width of at least 1 mm and having a thickness of at least 0.2 times and less than 0.75 times that of the thick region.

6. The ostomy device of claim 2 wherein the hydrocolloid adhesive further comprises a therapeutic material.

7. The ostomy device of claim 2 wherein the hydrocolloid adhesive further comprises one or more accelerators.

8. The ostomy device of claim 2 wherein the device further comprises a skin protective additive.

* * * * *